US00PP30764P3

(12) United States Plant Patent
Probasco et al.

(10) Patent No.: US PP30,764 P3
(45) Date of Patent: Jul. 30, 2019

(54) HOP PLANT NAMED 'HBC 692'

(50) Latin Name: *Humulus lupulus*
Varietal Denomination: HBC 692

(71) Applicant: HOP BREEDING COMPANY, L.L.C., Yakima, WA (US)

(72) Inventors: Eugene G. Probasco, Yakima, WA (US); Jason Perrault, Toppenish, WA (US)

(73) Assignee: Hop Breeding Company, L.L.C., Yakima, WA (US)

( * ) Notice: Subject to any disclaimer, the term of this patent is extended or adjusted under 35 U.S.C. 154(b) by 0 days.

(21) Appl. No.: 15/732,375

(22) Filed: Oct. 31, 2017

(65) Prior Publication Data

US 2018/0160598 P1 Jun. 7, 2018

Related U.S. Application Data

(60) Provisional application No. 62/496,944, filed on Nov. 1, 2016.

(51) Int. Cl.
*A01H 5/08* (2018.01)
*A01H 5/02* (2018.01)

(52) U.S. Cl.
USPC ..... Plt./236
CPC ..... *A01H 5/02* (2013.01)

(58) Field of Classification Search
USPC ..... Plt./236
CPC ... A01H 5/08; A01H 5/02; A01H 5/12; A01H 5/00; A01H 6/28; A01H 6/00
See application file for complete search history.

(56) References Cited

U.S. PATENT DOCUMENTS

PP29,577 P3 * 8/2018 Probasco ..... A01H 5/02 Plt./236

* cited by examiner

*Primary Examiner* — June Hwu
(74) *Attorney, Agent, or Firm* — Svendsen Legal, LLC

(57) ABSTRACT

A new hop plant named 'HBC 692' is disclosed. 'HBC 692' is used for its exceptional and unique aromatic qualities.

8 Drawing Sheets

Genus and species: *Humulus lupulus*.
Variety denomination: 'HBC 692'.

STATEMENT REGARDING FEDERALLY SPONSORED RESEARCH OR DEVELOPMENT

None

BACKGROUND OF THE INVENTION

'HBC 692' is a product of a controlled breeding program carried out by the inventors in the Yakima Valley of Washington State. 'HBC 692' was one of several seedlings resulting from an open pollination cross made in 2010 with female parent 'HBC 438' (U.S. Plant Pat. No. 29,577) and an unknown male parent. Seedling plants from this cross were planted in 2011 and screened for disease resistance and sex in a greenhouse and field nursery near Granger, Wash. A single plant of 'HBC 692' was selected in 2013. In 2014 'HBC 692' was expanded by asexual tissue culture propagation via softwood cuttings, to 14 plants in an evaluation block near Toppenish, Wash. The 'HBC 692' plants have now been observed and evaluated for several years. Throughout several generations of asexual propagation, 'HBC 692' has been observed to retain its distinctive characteristics and remain true to type.

COMPARISON OF 'HBC 692' TO PARENT PLANT AND COMARISON CULTIVAR

Table 1. below, sets forth some of the distinguishing characteristics of 'HBC 692' as compared to its female parent 'HBC 438', and to the 'Chinook' cultivar as a closely comparable cultivar.

TABLE 1:

| | INSTANT CV. 'HBC 692' | FEMALE PARENT 'HBC 438' | COMPARISON CV. 'CHINOOK' |
|---|---|---|---|
| Alpha (% of cone weight) | 8.9-10.4 | 14.5 | 11.5-15 |
| Beta (% of cone weight) | 8.1-10.2 | 5.8 | 3.0-4.0 |
| Co-humulone (% of alpha acids) | 37.6-39.0 | 22.6 | 27-31 |
| Total Oil (mL/100 g) | 3.6 | 2.95 | 1.0-2.5 |
| Aroma Profile | Citrus (pink grapefruit), fruity, pine, tropical, floral | Peachy, stone fruit, tropical, cedar, coconut | Grapefruit, spice, pine |

BRIEF DESCRIPTION OF THE PHOTOGRAPHS

Figure 1:
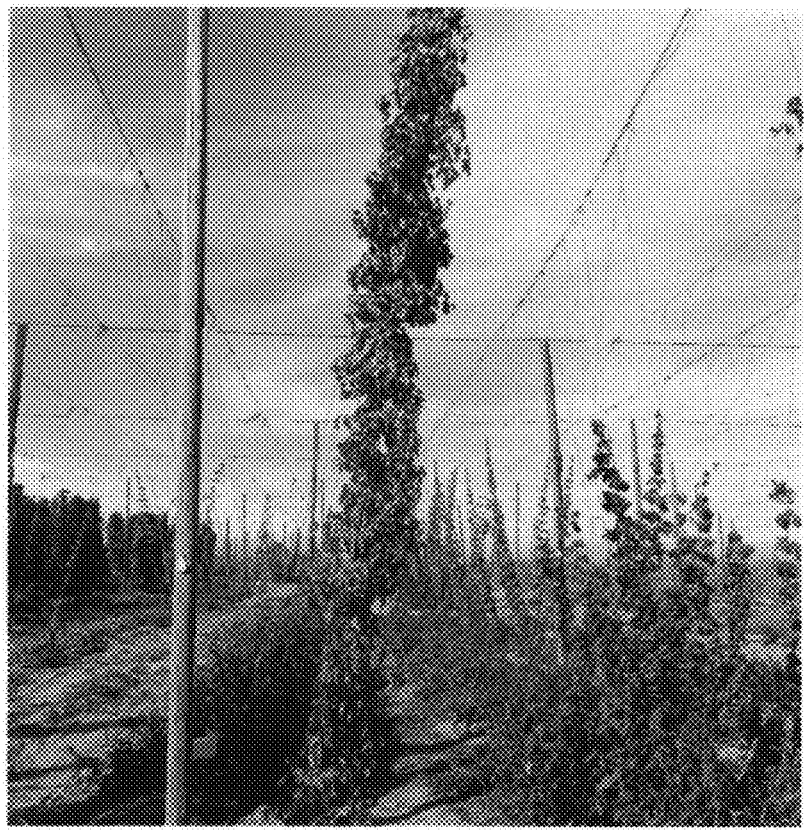
FIG. 1 illustrates a mature 'HBC 692' hop plant grown on a trellis.
Figure 2:
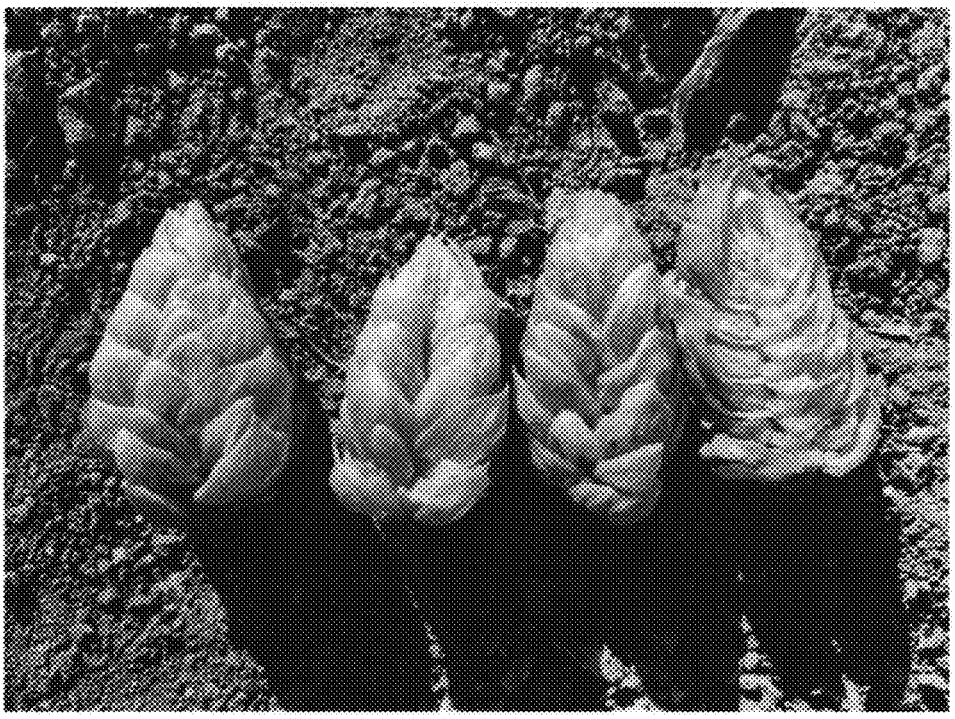
FIG. 2 illustrates whole cones and a cross section of a cone of the 'HBC 692' hop plant.
Figure 3:
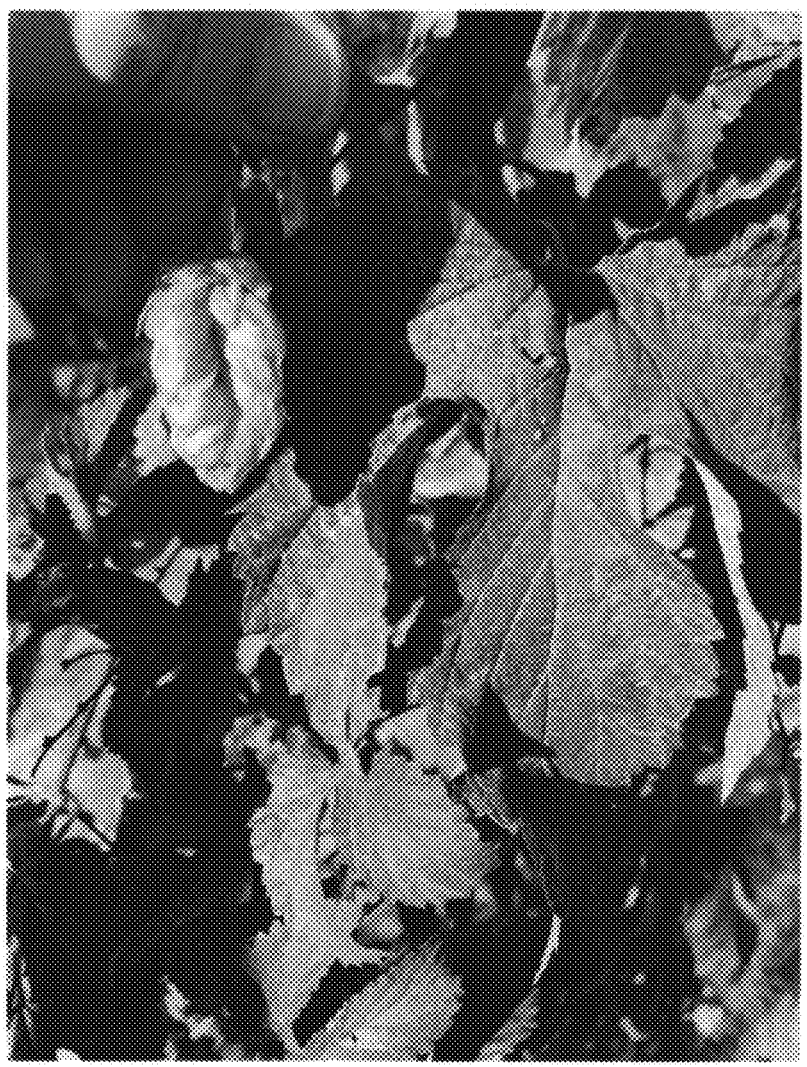
FIG. 3 illustrates cones and leaves on a mature 'HBC 692' hop plant.
Figure 4:
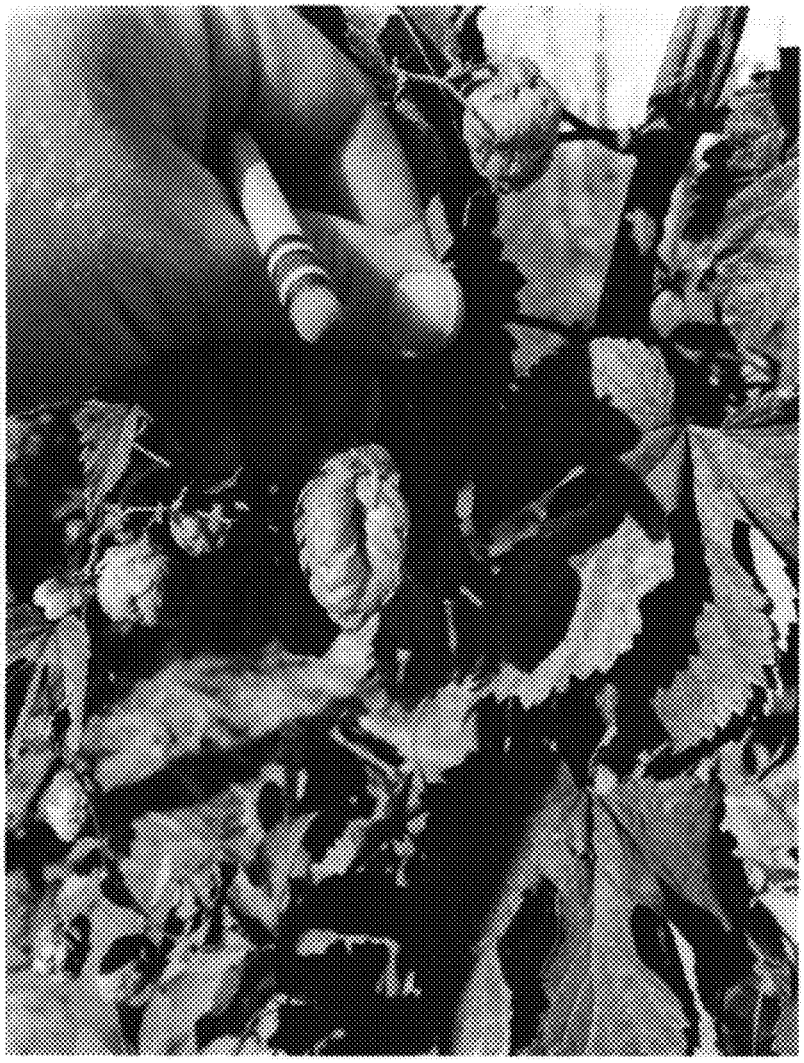
FIG. 4 illustrates cones and leaves on a mature 'HBC 692' hop plant.
Figure 5:
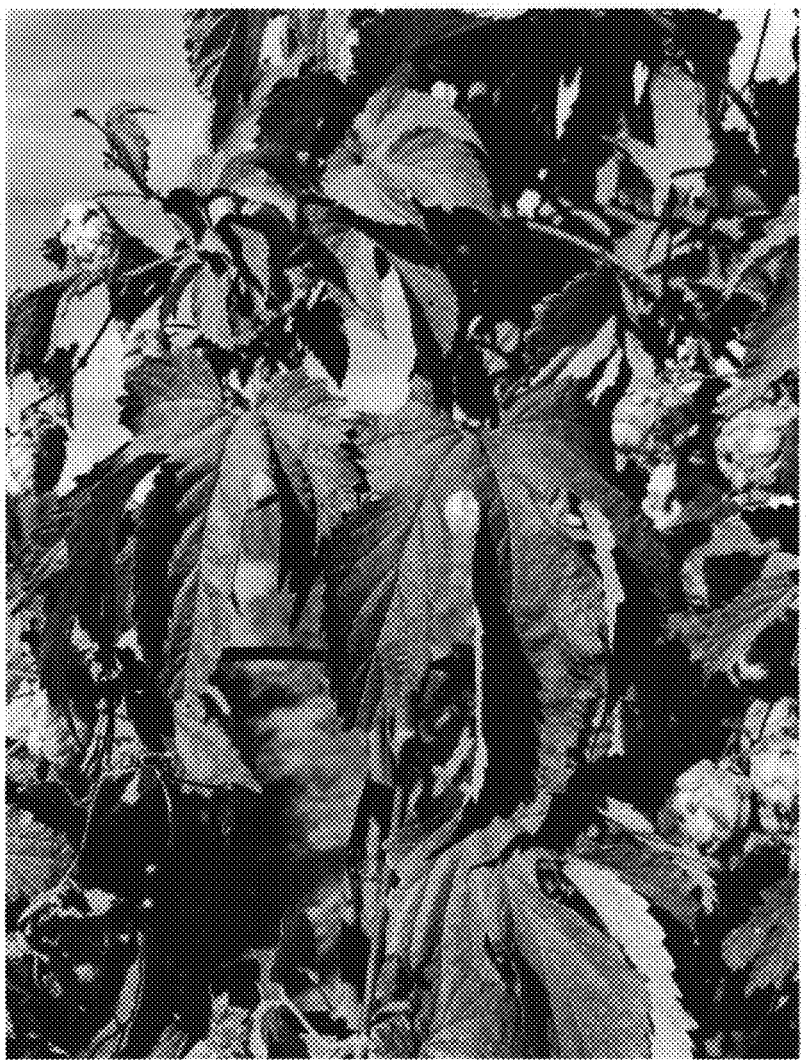
FIG. 5 illustrates leaves and cones on a mature 'HBC 692' hop plant.
Figure 6:
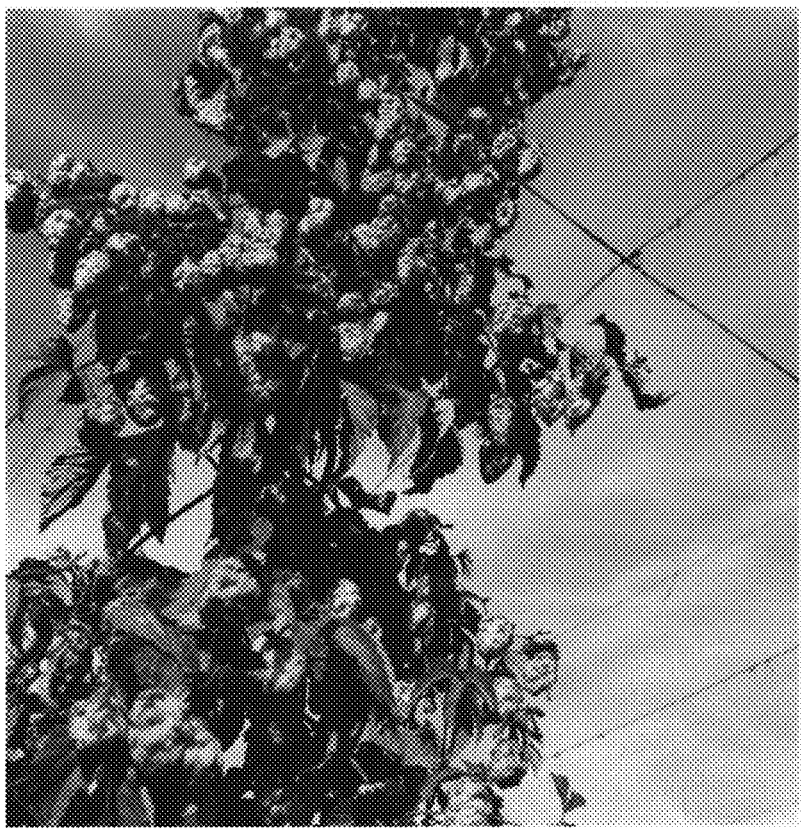
FIG. 6 illustrates cones and leaves of a mature 'HBC 692' hop plant.
Figure 7:
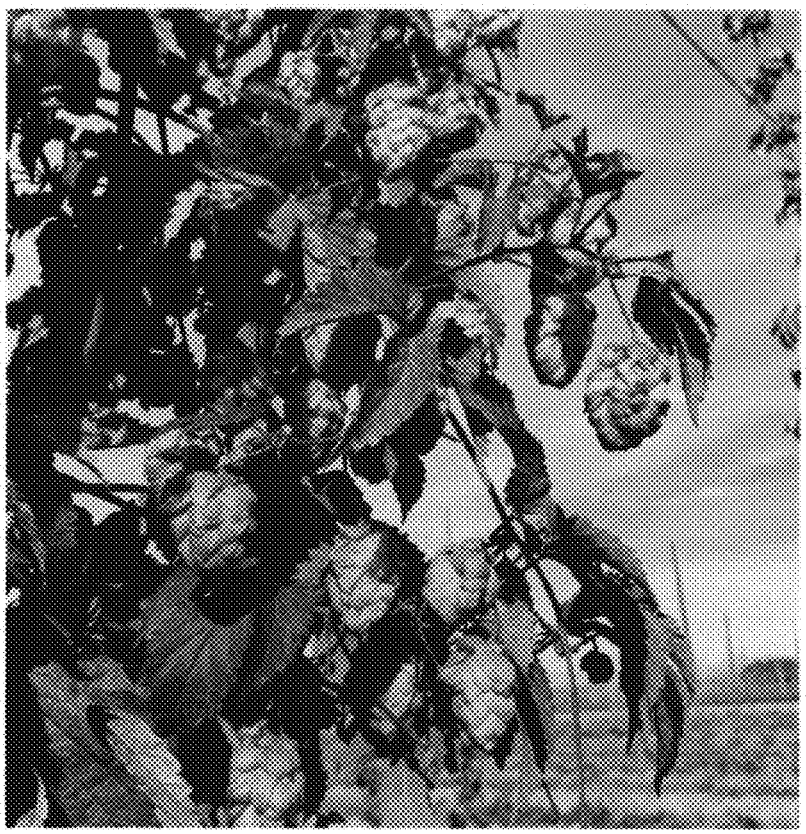
FIG. 7 illustrates cones on a mature 'HBC 692' hop plant.
Figure 8:
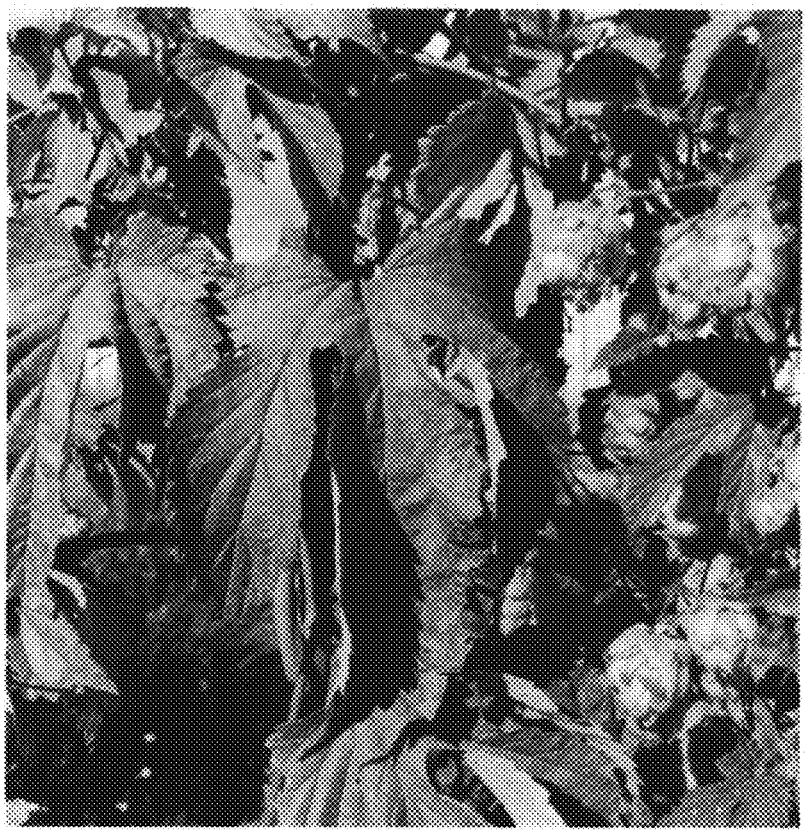
FIG. 8 illustrates leaves on a mature 'HBC 692' hop plant.

The colors of these illustrations may vary with lighting conditions and, therefore, color characteristics of this new variety should be determined with reference to the observations described herein, rather than from these illustrations alone.

DETAILED BOTANICAL DESCRIPTION

The following description is based on observations made during the 2016 growing season at Toppenish, Wash. It should be understood that the characteristics described will vary somewhat depending upon cultural practices and climatic conditions, and can vary with location and season. Quantified measurements are expressed as an average of measurements taken from a number of individual plants of the new variety. The measurements of any individual plant or any group of plants, of the new variety may vary from the stated average. All color references are based on the 2001 edition of The Royal Horticultural Society Colour Chart.

Ploidy: Diploid.

Sex: Female.

Use: Brewing beer and ale.

Harvest date: September 15 to 25 (during 2015 to 2016 growing seasons at Toppenish, Wash).

Yield: Average yield is 1800 kg/hectare to 2250 kg/hectare.

Disease reaction:

*Powdery Mildew.*—Susceptible.

*Downy mildew.*—Unknown.

*Verticillium wilt.*—Unknown.

TABLE 2

| Oil Analytical Characteristics (Averages): | |
|---|---|
| % Alpha Acid (% cone weight) | 8.9-10.4 |
| % Beta Acid (% cone weight) | 8.1-10.2 |
| % Cohumulone (% alpha acids) | 37.6-39.0 |
| Total Oil (ml/100 g of cones): | 3.6 |
| Hop Storage Index | <40.9%-57.7% |
| Aroma Profile | Citrus (pink grapefruit), fruity, pine, tropical, floral |
| A-Pinene: | 0.10% Total Oil |
| B-Pinene: | 0.91% Total Oil |
| Myrcene: | 56.77% Total Oil |
| 2-methyl-butyl isobutyrate: | 1.82% Total Oil |
| Limonene: | 0.21% Total Oil |
| Linalool: | 0.68% Total Oil |
| Caryophyllene: | 6.55% Total Oil |
| Farnesene: | 0.22% Total Oil |
| Humulene: | 16.14% Total Oil |
| Citral: | 0.20% Total Oil |
| Geranyl Acetate: | 0.06% Total Oil |
| Citronellol: | 1.25% Total Oil |
| Nerol: | 0.19% Total Oil |
| Geraniol: | 1.67% Total Oil |
| B-lonene: | 0.00% Total Oil |

Plant growth type: Climbing Bine, Normal (not dwarf), Cylindrical.

Anthocyanin coloration of bine: Weak to Medium.

Hardiness: Observed Plant Hardiness Zone 7a.

Freeze tolerance: Typically intolerant of freezing temperatures during the growing season.

Bine:

*Color.*—Yellow-Green 144A.

*Stripe present.*—Yes.

*Stripe color.*—Red-Purple 59A.

*Stipule direction.*—Up.

*Average number of stipule per bine.*—Two per node.

*Stipule color.*—Yellow-Green 144A.

*Bine diameter.*—7.6 mm at base; 80 mm at nine feet; 5.8 mm at terminal end of eighteen feet.

*Typical and observed bine length.*—Typical bine growth of 18 feet to 25 feet, when grown on a standard eighteen foot trellis.

Lateral:

*Lateral length.*—On average, 30.5 cm to 91.5 cm.

*Lateral density.*—2 laterals per/node.

Leaf:

*Arrangement.*—Opposite.

*Shape.*—Palmately Lobed.

*Average length of mature leaf.*—13.3 cm.

*Average width of mature leaf.*—17.1 cm.

*Color of mature leaf upper surface.*—Green 137A.

*Color of mature leaf lower surface.*—Yellow-Green 147B.

*Color of immature leaf upper surface.*—Green 137A.

*Color of immature leaf lower surface.*—Yellow-Green 147B.

*Number of lobes.*—3 to 5.

*Margin.*—Serrate.

*Serrations per inch.*—4 to 5.

*Average petiole length (mature).*—83 mm.

*Petiole color at base.*—Greyed-Purple 187B.

*Venation.*—Palmate.

*Vein color.*—Yellow-Green 145B.

Cone:

*Avg. length.*—36 mm.

*Avg. diameter.*—20 mm.

*Bract tip color.*—Yellow-Green 144A.

*Bract base color.*—Yellow-Green 145B.

*Bracteole color.*—Yellow-Green 145B.

*Cone shape.*—Ovate.

*Cone tip shape.*—Acute.

*Average cone weight.*—800 mg to 1100 mg.

*Bract shape.*—Orbicular.

*Bract tip shape.*—Acuminate-Mucronate.

*Bract tip position.*—(Not observed).

*Bract average length.*—17 mm to 18 mm.

*Bract average width.*—11 mm to 14 mm.

*Bracteole average length.*—8 mm to 11 mm.

*Bracteole average width.*—4 mm to 7 mm.

*Bracteole shape.*—Ovate.

*Observed appearance of female inflorescences.*—Middle to Late July.

*Pickability.*—Good.

*Lupulin glands color.*—Yellow 2A.

The invention claimed is:

1. A new and distinct Hop plant as illustrated and described herein.

* * * * *